United States Patent
Lachance et al.

(10) Patent No.: US 11,324,621 B2
(45) Date of Patent: May 10, 2022

(54) SUPPORTIVE BELT ASSEMBLY FOR LOWER EXTREMITY ORTHOTIC DEVICES

(75) Inventors: Geneviève Lachance, Québec (CA); Stéphane Bédard, St-Auqustin-de-Desmaures (CA)

(73) Assignee: B-temiA Inc., St-Augustin-de-Desmarues (CA)

( * ) Notice: Subject to any disclaimer, the term of this patent is extended or adjusted under 35 U.S.C. 154(b) by 0 days.

(21) Appl. No.: 14/004,639

(22) PCT Filed: Mar. 21, 2012

(86) PCT No.: PCT/CA2012/000310
§ 371 (c)(1),
(2), (4) Date: Dec. 19, 2013

(87) PCT Pub. No.: WO2012/126104
PCT Pub. Date: Sep. 27, 2012

(65) Prior Publication Data
US 2014/0094729 A1    Apr. 3, 2014

Related U.S. Application Data

(60) Provisional application No. 61/454,632, filed on Mar. 21, 2011.

(51) Int. Cl.
*A61F 5/01* (2006.01)

(52) U.S. Cl.
CPC .............. *A61F 5/01* (2013.01); *A61F 5/0102* (2013.01)

(58) Field of Classification Search
CPC .................. A61F 5/0102; A61F 5/0193; A61F 2005/0183; A61F 2005/0181; A61F 5/0104; A61F 2005/0132–0179; A61F 2005/0193; A61F 5/022–05891; A61F 5/24–34; A61F 5/01–028; A61H 1/0237–0266; A61H 1/02–0266; A61H 3/00–008; A62B 35/00–0037
USPC ....................................... 602/16, 23
See application file for complete search history.

(56) References Cited

U.S. PATENT DOCUMENTS

| | | | | |
|---|---|---|---|---|
| 170,656 A | * | 12/1875 | Allen | A61F 5/028 602/19 |
| 1,336,695 A | * | 4/1920 | Gromes | A61F 5/0102 473/217 |
| 2,654,365 A | * | 10/1953 | Whitaker | A61F 5/0102 602/16 |
| 4,557,257 A | * | 12/1985 | Fernandez | A61F 5/0102 602/19 |
| 5,054,476 A | * | 10/1991 | Petrofsky | A61F 5/0125 602/16 |

(Continued)

*Primary Examiner* — Michelle J Lee
(74) *Attorney, Agent, or Firm* — Praxis

(57) ABSTRACT

A multi-segment supportive belt assembly for reducing displacement of one or more orthotic devices on the lower extremities of a user. The supportive belt comprises a first group of segments including a plurality of linking segments linking the supportive belt assembly to the anatomical structure of the user, and a second group of segments including, for each lower extremity, at least one lateral segment connecting adjacent linking segments, the at least one lateral segment being longitudinally aligned with the user's hips, at least one of the lateral segments being adapted to be connected to the one or more orthotic devices.

15 Claims, 3 Drawing Sheets

(56) References Cited

U.S. PATENT DOCUMENTS

| | | | | |
|---|---|---|---|---|
| 5,144,943 A | * | 9/1992 | Luttrell | A61F 5/0111 601/33 |
| 5,429,588 A | * | 7/1995 | Young | A61F 5/0127 36/28 |
| 5,718,672 A | * | 2/1998 | Woodman | A61F 5/0193 602/23 |
| 5,961,476 A | * | 10/1999 | Betto | A61F 5/0102 482/51 |
| 6,039,707 A | * | 3/2000 | Crawford | A61F 5/0193 602/18 |
| 6,050,962 A | * | 4/2000 | Kramer | A61B 5/1071 600/595 |
| 6,540,703 B1 | * | 4/2003 | Lerman | A61F 5/0193 602/16 |
| 6,589,195 B1 | * | 7/2003 | Schwenn | A61F 5/0125 602/16 |
| 2012/0095379 A1 | * | 4/2012 | Hama | A61F 5/0193 602/23 |

\* cited by examiner

US 11,324,621 B2

SUPPORTIVE BELT ASSEMBLY FOR LOWER EXTREMITY ORTHOTIC DEVICES

CROSS-REFERENCE TO RELATED APPLICATIONS

This application claims the benefits of U.S. provisional patent application No. 61/454,632 filed on Mar. 21, 2011, which is herein incorporated by reference.

TECHNICAL FIELD

The present disclosure relates to a supportive belt assembly for lower extremity orthotic devices.

BACKGROUND

One of the major functional issues with lower extremity orthotic devices is the physical stability of the device on the user's leg. During its use, a lower extremity orthotic device such as a knee brace tends to displace itself in various directions away from its main pivotal references, i.e. its respective natural axes of rotation. These displacements significantly reduce the efficiency of the orthotic device and even worse, a misalignment of the device with regard to its natural axes of rotation can lead to acute and chronic injuries. In fact, misalignments arising from the displacement of the device from its original position reduce its capability to adequately stabilize the respective joint-segment body structure and, in the case of a powered orthotic device, its ability to transfer additional biomechanical forces to the body. As a consequence, users often use homemade means to try to roughly secure the positioning of their brace with the goal of minimizing its displacement and optimizing its functionality.

Manufacturers have tried to improve and upgrade the attachment systems of orthotic devices in order to properly secure their biomechanical positioning. The more recent attachment mechanisms are efficient for a certain period of time and for confined conditions of use. Unfortunately, they lose their efficiency when used for an extended duration and/or when the fitting conditions at the structural interface change for any reasons such as the onset of a certain amount of perspiration. Extreme mobility is also a major factor that provokes such displacements of orthotic devices.

Accordingly, there is a need for a support mechanism for orthotic devices that eliminates undesired displacements.

SUMMARY

The present disclosure provides a multi-segment supportive belt assembly for reducing displacement of one or more orthotic devices on the lower extremities of a user, comprising:
a first group of segments, including:
a plurality of linking segments linking the supportive belt assembly to the anatomical structure of the user; and
a second group of segments, including, for each lower extremity:
at least one lateral segment connecting adjacent linking segments, the at least one lateral segment being longitudinally aligned with the user's hips, at least one of the lateral segments being adapted to be connected to the one or more orthotic devices;
wherein the multi-segment belt assembly reduces undesired longitudinal, rotational and shifting displacements of the one or more orthotic devices on the lower extremities of the user.

The present disclosure also provides a multi-segment supportive belt assembly wherein the first group of segments includes:
a first linking segment located at the user's waist level transferring part of the load generated by the one or more orthotic devices to the user's pelvic bone;
a second linking segment located at the user's gluteal level transferring part of the load generated by the one or more orthotic devices to the user's gluteal muscles; and
a third linking segment located at the user's thighs proximal end level transferring part of the load generated by the one or more orthotic devices to the user's thighs proximal ends.

The present disclosure further provides a multi-segment supportive belt assembly wherein the second group of segments, includes, for each lower extremity:
a first lateral segment that flexibly connects the first linking segment and the second linking segment; and
a second lateral segment that rigidly connects the second linking segment and the third linking segment, the second lateral segment being adapted to be connected to the one or more orthotic devices.

BRIEF DESCRIPTION OF THE FIGURES

Embodiments of the disclosure will be described by way of examples only with reference to the accompanying drawings, in which.

DETAILED DESCRIPTION

Generally stated, the non-limitative illustrative embodiment of the present disclosure provides a supportive belt assembly for lower extremity orthotic devices that eliminates, or at least greatly reduces, undesired displacements of the orthotic devices. The supportive belt assembly is a multi-segment belt assembly worn by the user at the waist and hip level, to which are attached one or more orthotic devices. Thus attached, the longitudinal and the rotational mobility of the orthotic device is restricted by the capacity of the supportive belt assembly to limit, even eliminate, undesirable shifting.

The supportive belt assembly enhances the stability of lower extremity orthotic devices on a user and, in the case where the orthotic devices are powered, (i.e. can generate biomechanical efforts at the joints), the quality of the force transfer from the lower extremity orthotic devices to the user's limbs.

The design of the supportive belt assembly is based upon the concept of the waist as an anchoring central point.

Figure 1:
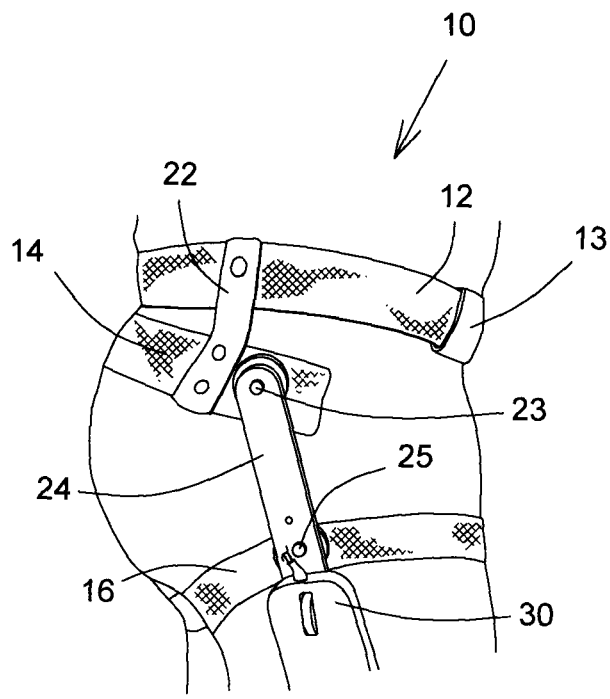
FIG. 1 is a side view of the supportive belt assembly in accordance with an illustrative embodiment of the present disclosure.
Figure 2:
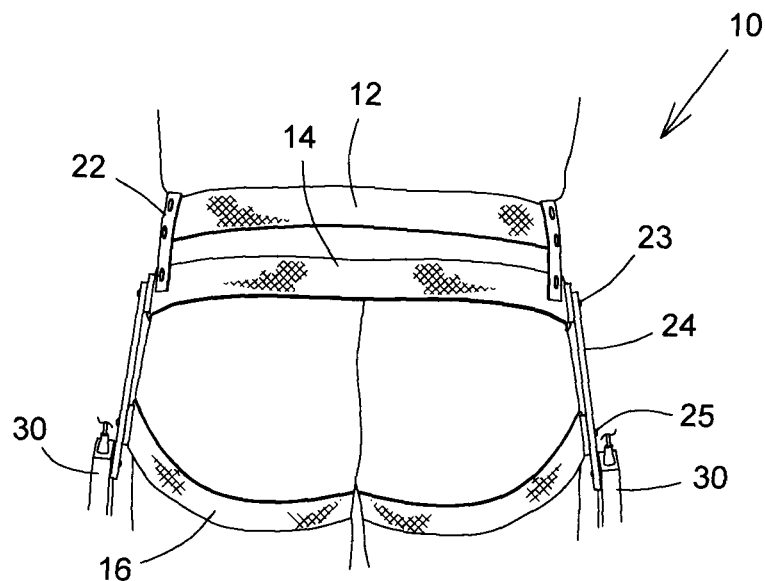
FIG. 2 is a back view of the supportive belt assembly of FIG. 1.

Referring to FIGS. 1 and 2, the supportive belt assembly 10 comprises six major components separated in two groups: a linking segments group and a lateral segments group. The linking segments group includes a waist belt 12, a lower-back hips belt (LBHB) 14 and upper thigh contact areas 16, while the lateral segments group includes, on each side of the body of the user, a flexible lateral segment 22 that links the waist belt 12 and the LBHB 14, and a rigid lateral segment 24 that links the LBHB 14 and the upper thigh contact areas 16.

The components 12, 14, 16, 22 and 24 of the supportive belt assembly 10 are grouped with respect to their function into the assembly. The linking segments group (12, 14, 16) gathers together components characterized as supportive elements. Components of this first group are of high importance to deliver the assistive capacities of the orthotic devices to the user. The lateral segments group (22, 24) gathers components used to connect together the first group's supportive components.

Each component of the linking segment group (12, 14, 16) is a direct connection to the human anatomical structure: the waist belt 12 to the waist level transferring part of the load generated by the orthotic devices to the user's pelvic bone; the LBHB 14 to the gluteal level transferring part of the load generated by the orthotic devices to the user's gluteal muscles; and the upper thigh contact areas 16 to the thighs proximal end level transferring part of the load generated by the orthotic devices to the user's thighs proximal ends (i.e. lower buttocks). As can be seen in FIG. 1, the waist belt 12 is worn at the waist level and closed by a frontal buckle 13. Supportive elements have as primary function of creating a mechanical human-machine interface so as to connect to the mechanical bones and muscles structures as directly as possible. The efficiency of this mechanical human-machine interface to stabilize the orthotic devices 30 and/or to transfer forces to users has a direct impact on orthotic devices assistive capacities.

Components of the lateral segments group (22, 24) are used to connect together the supportive elements, i.e. 12, 14 and 16. Each flexible lateral segment 22 links the waist belt 12 with the LBHB 14. The flexible lateral segment 22 is important to unconstrain hip movements of the user. The rigid lateral segments 24 links tips the LBHB 14, via pivot 23, to the upper thigh contact areas 16 and tip of the frame of the orthotic device 30, via pivot 25.

The purpose of the supportive belt assembly 10 can be summarized in three points: provide vertical stability, provide torsional stability and force transfer.

Vertical Stability

Figure 3:
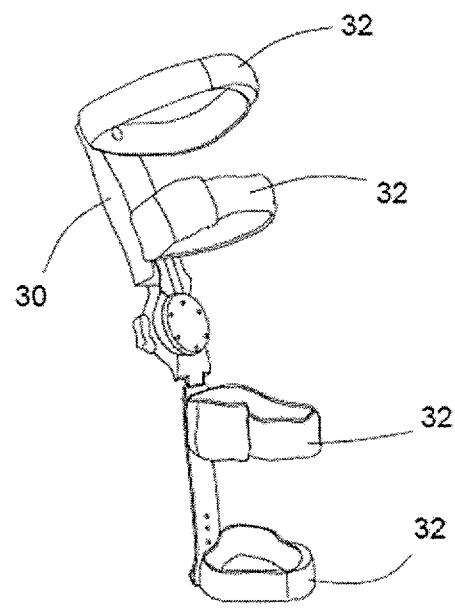
FIG. 3 is a perspective view of an orthotic device.

The conical shape of the human legs (i.e. lower extremities) allows the orthotic device 30 to easily slip downward on the leg under its weight. Referring to FIG. 3, the four attachment points 32 of the orthotic device 30 are not sufficient to keep the orthotic device 30 in place in a comfortable manner, neither in movement nor in static position.

Accordingly, one objective of the supportive belt device 10 is to keep the orthotic device 30 in place, vertically, onto the leg of the user, in order to stabilize the orthotic device 30 and/or to transfer part of the load of the orthotic device 30 to the waist of the user.

Torsional Stability

Muscular surfaces onto which the orthotic device 30 lies are more or less firm, depending on the user and on the type of activity carried out. For powered orthotic devices generating biomechanical efforts at their motorized joints, the efficiency of the forces transferred from the joint mechanisms and the body segments is reduced by the fact that a part of these additional forces are lost into muscular tissues before providing the expected level of assistance. Repeated displacements of the orthotic device 30 on the leg result in the rotation of the orthotic device 30 around the leg of the user, moving inwardly and causing potential skin lesions.

Accordingly, another objective of the supportive belt assembly 10 is to keep the orthotic device 30 in place in order to prevent it from rotating around the leg of the user.

Force Transfer

In addition to being uncomfortable, the compression of soft tissues at the upper thigh contact areas significantly decreases the efficiency of the assistance provided by the orthotic device 30. Hysteresis introduced by the displacement of the orthotic device 30 on the surface of the leg of the user (i,e, the delay that the additional forces generated by the powered orthotic device take to be effectively transferred to the body segment) is not desirable because it lowers the efficacy of the mobility assistance to the user.

Accordingly, a further objective of the supportive belt assembly 10 is to keep the orthotic device 30 in place to prevent the contact areas 32 of the orthotic device to be pushed into the soft tissues of the leg of the user.

Each component of the linking segments group (12, 14, 16) and the lateral segments group (22, 24) will now be described further, describing their physical structure, their function as well as how each component contributes to reach the stability and force enhancement objectives described above.

Linking Segments Group

Waist Belt

With reference to FIGS. 1 and 2, the waist belt 12 in the illustrative embodiment is about 5 cm in width and is closed by a frontal buckle 13 (see FIG. 1). The inward surface of the waist belt 12 is covered with Velcro™ loops compatible with potential Velcro™ hooks on the pants of the user to limit undesired movements of the waist belt 12. Tips of the inward surface of the waist belt 12 have Velcro™ hooks which allow an easy adjustment to the waist measurement of the user. The waist belt 12 is made of two thick polypropylene straps sewed together, resulting in a high rigidity cross section, able to resist in vertical planes to torsion efforts applied by the weight of the orthotic device 30. The waist belt 12 cross section rigidity is required to prevent local deformation of the belt causing considerable discomfort to the user. Each orthotic device 30 is linked to the waist belt 12 by the mean of a flexible lateral segment 22 that connects the waist belt 12 and the LBHB 14.

The pelvis bone offers a solid structure for a comfortable and even distribution of orthotic device 30 load. The waist belt 12 transfers part of the load from the orthotic devices 30, approximate 1.5 kg each, to the waist of the user through its flexible lateral segment 22. Thus, downward displacement of the orthotic devices 30 is prevented, and vertical stability objective is reached.

Furthermore, assistance forces can be transferred to the waist of the user, offering an additional point of contact between the orthotic devices 30 and the user and improving the efficacy of force transfer.

Lower Back-Hips Belt (LBHB)

With reference to FIGS. 1 and 2, the role of the LBHB 14 is to provide the rigid lateral segment 24 a fixed position where to be attached at the waist. Since free rotations in the sagittal plane are required for all hips' movements, the LBHB 14 is connected to the frame of the orthotic device 30 via pivots 23 and 25 of the rigid lateral segment 24. This mechanical parts assembly lets the hips' joints free to move while providing a firm attachment to the user's waist.

The LBHB 14 in the illustrative embodiment is made of a strong and thick polypropylene weaving of about 5 cm in width that can resist substantial torsion efforts. It has to be flexible to conform to the lower back shape during assisting phases so as to offer a surface of contact as large as possible; the largest the surface of contact the more evenly is the load distributed on the user's waist, resulting in a direct comfort improvement. Fitting holes are provided on each side, accommodating various waist sizes. For example, the LBHB 14 can be provided with eight fitting holes accommodating waist sizes from about 71 cm to 101 cm. Pivots 23 and 25 are attached to the LBHB 14 and the frame of the orthotic device 30 through these holes by mean of a mechanical bolt and nut pivot, or any other such attachment.

The purpose of the LBHL 14 is to keep in place the upper ends of the orthotic devices 30 and to offer a force transfer contact area independent of the waist belt 12.

It can be observed that the LBHB 14 has no forward section. The purpose of the absence of a forward section is to eliminate antero-posterior constraints on pivot 23. Pivot 23 is advantageously located above and a little behind the natural hip joint; in which case, a lever of force is created above the mechanical pivot point. For all forward legs movements (crouching, sitting, large forward strides, etc.), this lever of force may cause a frontal section to press into the lower abdomen, and thus be an important source of discomfort for the user. For that reason, the LBHB 14 only possesses a rear section. This also explains why the waist belt 12 is minimally connected to the LBHB 14. The use of a flexible lateral segment 22 in-between the waist belt 12 and the LBHB 14 offers a force transfer contact area independent of the waist belt 12, and guarantees that no over straining efforts are put on the lower abdomen.

The attachment point between the LBHB 14 and the upper end of the orthotic device 30 via pivot 25 is located as near as possible to the natural hip joint in the vertical axis. In the horizontal plane, this point is specifically located at the front or a little behind the natural hip joint. It is essential for stability purposes that the point of attachment does not overpass the natural hip joint. During the assisting phases, the LBHB 14 is pressed on the lower back of the user and the position of the attachment point prevents the upper end of the orthotic device 30 from moving forward. Preventing forward displacement as well as displacement around the leg result in a direct stability increase (i.e. torsional stability).

Also, since the LBHB 14 is being pressed onto the firm lower back and pelvis bone structures, less hysteresis is observed during the first few moments of assisting phases. The quality of force transfer is thus significantly improved.

Upper Thigh Contact Areas

Figure 4:
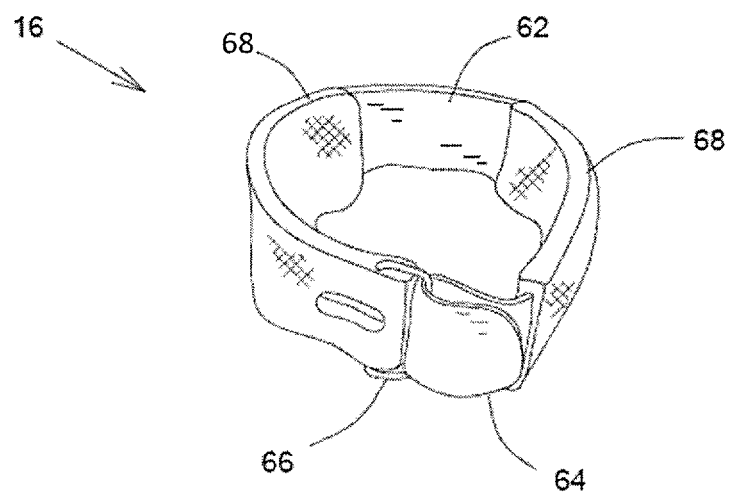
FIG. 4 is a perspective view of the upper thigh contact area.

With reference to FIGS. 1, 2 and 4, the upper thigh contact areas 16 allow the transfer of forces from the orthotic device 30 to the proximal end of the user's thighs. In the illustrative embodiment, the upper thigh contact areas 16 are made of urethane reinforced with a carbon fiber mattress and have rounded shape in order to provide a high level of comfort to the user. A polypropylene Velcro™ restraining strap 62 surrounds the leg. The doubled sided Velcro™ is used as closing system 64 to lock the upper thigh contact areas 16 onto each leg. The tips 66 of the upper thigh contact areas 16 each include a groove in order to attach the restraining strap. Neoprene cushions 68 are implemented onto the straps to improve user comfort. The "stickiness" characteristic of neoprene material strengthens the resistance to torsion forces in the transversal plane.

In order to provide a better fit for different user morphologies, each upper thigh contact area 16 is fully adjustable in the sagittal plane: two degree of freedom in translation which can be locked into place, and one degree in rotation, kept free at all time. The vertical translation is possible by means of multiple holes made in the upper brace segment; allowing adjustments for different user heights. The antero-posterior translation allows fitting to the user's segment diameter by means of a groove made in the backward tip of the upper thigh contact areas 16. The rotation in the sagittal plane is left free to leave user's leg free to move while improving the user's comfort.

The upper thigh contact areas 16 are specifically located at the buttocks and hamstring muscles junction. This anatomical area is quite close to the pelvic bone structure and consequently reduces compression of soft tissues and undesired orthotic device 30 displacement. The efficacy of force transfer by orthotic devices 30 is then improved, as well as the general user comfort.

The positioning of the upper thigh contact areas 16 also serves as an anchoring point for the other components of the supportive belt assembly 10, improving the fit onto the user's waist and enhancing the general stability of the orthotic devices 30.

Lateral Segments Group

Flexible Lateral Segment

With reference to FIGS. 1 and 2, the flexible lateral segment 22 in the illustrative embodiment takes the form of a polypropylene band of a width of about 2.5 cm, linking the waist belt 12 to the LBHB 14 above pivot 23.

The main objective of the flexible lateral segment 22 is to transfer the load from the orthotic device 30 to the waist belt 12; the flexible lateral segment 22 is actually used to accomplish the load transfer function from the orthotic device 30 when it is put under tension.

Torso lateral movements have to be comfortable and free of constraints above the human hip joint. Accordingly, the flexibility characteristic of the flexible lateral segment 22 avoids the undesired situation of having a rigid lateral segment above the human hip joint pushed into torso flesh during transversal plane torso rotations.

Rigid Lateral Segment

With reference to FIGS. 1 and 2, the rigid lateral segment 24 in the illustrative embodiment takes the form of a 6061-T6 aluminum strip of a width of about 3.8 cm. The rigid lateral segment 24 links pivot 23 to the proximal upper end of the frame of the orthotic device 30 by means of bolts or other such attachment. The function of the rigid lateral segment 24 is to link pivots 23 and 25 of the upper thigh contact areas 16. Both supportive elements, the LBHB 14 (positioned through pivot 23) and the upper thigh contact areas 16 (positioned through pivot 25) serve as anchoring elements for the orthotic device 30 in order to transfer assisting force to the user. The positioning of pivot 23 on the transversal plane prevents the orthotic device 30 from moving around the user's limbs during assisting phases.

The rigid lateral segment 24 is provided with holes allowing for length adjustments, which as a result positions pivots 23 and 25 of the upper thigh contact areas 16. The closer pivot 23 is to the actual human hip joint, the more efficient and comfortable will be the supportive belt assembly 10.

Deficiencies in stability and force transfer are noticeably reduced using the supportive belt assembly 10, and the biomechanical benefits directly result in a gain in comfort for the user. Components making up the supportive belt assembly 10 thus provide orthotic devices 30 with a firm and solid anchoring point, allowing the user to get the most out of each orthotic device's 30 assisting capabilities.

Mechanical Hip Joint (MHJ)

Figure 5:
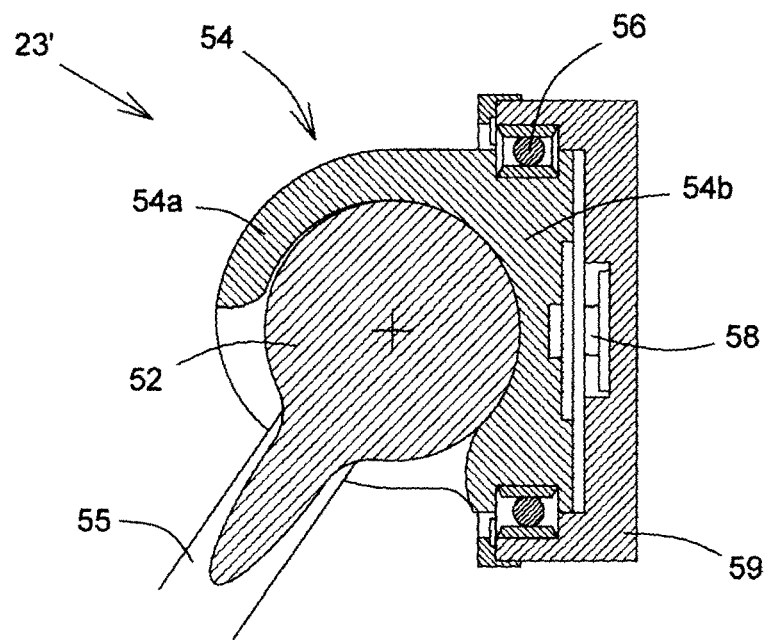
FIG. 5 is a cross-sectional view of a mechanical hip joint.
Figure 6:
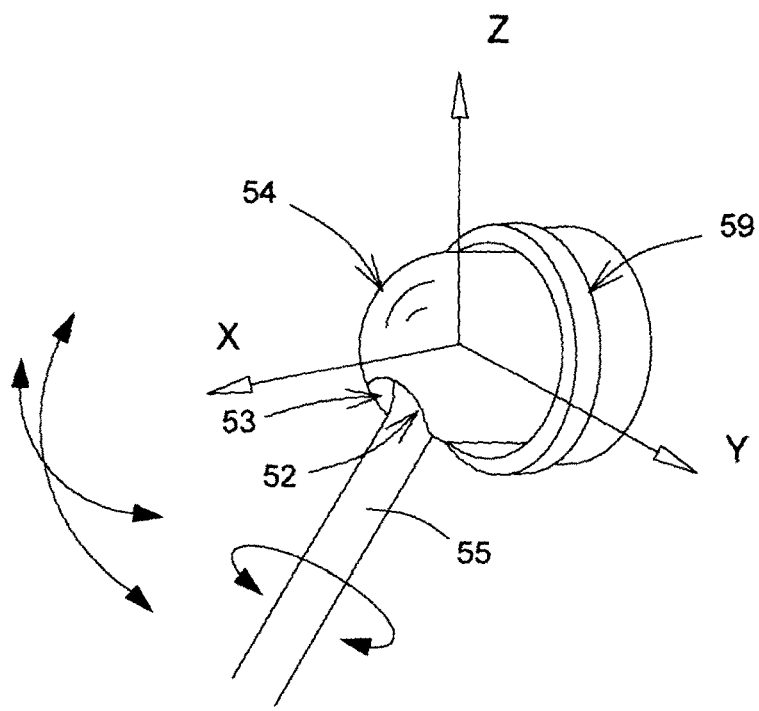
FIG. 6 is a perspective view of the mechanical hip joint.

With reference to FIGS. 5 and 6, there is shown an illustrative embodiment of a mechanical hip joint (MHJ) 23' that may be used in replacement of pivot 23 (see FIGS. 1 and 2) in an alternative embodiment of the supportive belt assembly 10 or used with other orthotic or robotic devices. The MHJ 23' consist in a ball joint like mechanism having as a primary function the unconstraining of the pelvis and hips movements. The ball joint like mechanism is composed of five main components: an anodized aluminum sphere 52 with and elongated member portion 55, a two piece (54a and 54b) capsule 54, a reduced cross section ball bearing 56, an optional angular position sensor 58 and a housing 59. The housing 59 is attached to the LBHB 14, the capsule54 being rotatably connected to the housing 59 via the reduced cross section ball bearing 56. The sphere 52 is positioned inside the capsule 54 and its elongated member portion 55 forms the rigid lateral segment 24, protruding from the capsule 54 through groove 53.

The human hip can execute movements with respect to the three rotational axes. Leaving the user's movements unconstrained requires the MHJ 23' to mimic the three decoupled natural hip rotations. Referring to FIG. 6, the vertical rotation (Z-transverse plane) is allowed by the sphere 52, rotating vertically inside its capsule 54. The frontal rotation (Y-transverse plane) is made possible through a groove 53 made perpendicularly with respect to the sagittal plane. The MHJ 23' allows the user to move its legs sideward, i.e. sagittal rotation (X-transverse plane), from an angle of about 90 degrees in abduction to an angle of about 10 degrees in adduction. It is the groove 53 that decouples the frontal rotation axis (Y-transverse plane) from the sagittal rotation axis (X-transverse plane). The groove 53 prevents the sphere 52 from rotating inside its capsule 54 during sagittal axis rotations. It is then the capsule 54 itself that rotates, through the action of the ball bearing 56, with respect to the housing 59. This third rotation can be monitored with an optional sensor, for example a magnetic angular position sensor, for artificial intelligence purposes.

All degrees of adjustment and degrees of freedom are addressed: circumferential localization of MHJ 23' on the waist is possible; abduction and adduction movements are not restrained; and the three natural rotations are let free and decoupled. The MHJ 23' is then used as a link between the LBHB 14 and the upper end of orthotic devices 30 to leave unconstrained natural pelvis' and hips' movements. The unconstraining action of this mechanism allows the LBHB 14 and orthotic devices 30 to stay fixed onto user's waist and legs, resulting in a major stability improvement.

The MHJ 23' also links the orthotic device 30 to the waist belt 12, allowing the load to be properly distributed to the waist belt 12 without over constraining pelvis' and hips' movements.

It is to be understood that the various components of the supportive belt assembly 10 have been described in accordance with illustrative embodiments of the present disclosure and that the material used, as well as their dimensions, may vary depending, for example, on the application and/or the size of the user.

Although the present disclosure has been described by way of particular non-limiting illustrative embodiments and examples thereof, it should be noted that it will be apparent to persons skilled in the art that modifications may be applied to the present particular embodiment without departing from the scope of the present disclosure.

We claim:

1. A multi-segment supportive belt assembly for reducing displacement of one or more orthotic devices on lower extremities of a user, com prising:
   a first group of segments, including:
   a first linking segment configured to be positioned at the user's waist level for transferring part of a load generated by the one or more orthotic devices to the user's pelvic bone;
   a second linking segment configured to be positioned at the user's gluteal level for transferring part of the load generated by the one or more orthotic devices to the user's gluteal muscles, the second linking segment having a first and second opposed extremities provided with respective pivots and configured to terminate on each side of the user's hip joints;
   a pair of third linking segments configured to be positioned at and encircle a respective user's thigh proximal end at a buttocks and hamstring muscles junction for transferring part of the load generated by the one or more orthotic devices to the user's thighs proximal ends, each of the pair of third linking segments having a pivot and being formed by a restraining strap with cushions implemented thereon;
   a second group of segments, including, for each lower extremity:
   a pair of first flexible lateral segments connecting the first linking segment and the second linking segment, each of the first lateral segments being configured to extend between the waist and respective hip of the user;
   a pair of second rigid lateral segments connecting the second linking segment and the third linking segments directly via the respective pivots of the second linking segment and the third linking segments, each of the second lateral segments being configured to extend between the respective hip and the respective thigh proximal end of the user, and being adapted to be connected to the one or more orthotic devices; wherein each of the pair of second rigid lateral segments are formed by a singular rigid strip.

2. A multi-segment supportive belt assembly in accordance with claim 1, wherein each of the third linking segments includes upper thigh contact areas.

3. A multi-segment supportive belt assembly in accordance with claim 2, wherein the upper thigh contact areas are adjustable in the sagittal plane.

4. A multi-segment supportive belt assembly in accordance with claim 3, wherein the upper thigh contact areas are adjustable with two degrees of freedom in translation and one degree of freedom in rotation.

5. A multi-segment supportive belt assembly in accordance with claim 1, wherein the pivots connecting the second lateral segments to the second linking segment consist in ball joint mechanisms.

6. A multi-segment supportive belt assembly in accordance with claim 5, wherein each of the ball joint mechanisms is composed of a housing attached to the second linking segment, a capsule rotatably connected to the housing, a sphere positioned inside the capsule, the sphere having an elongated member portion forming the respective second lateral segment and protruding from the capsule through an elongated groove.

7. A multi-segment supportive belt assembly in accordance with claim 6, wherein the housing includes an angular position sensor.

8. A multi-segment supportive belt assembly in accordance with claim 1, wherein the second linking segment is flexible.

9. A multi-segment supportive belt assembly in accordance with claim 8, wherein the second linking segment is made of a weaving configured to resist torsion efforts, the flexibility of the second linking segment allowing it to conform to a body shape of the user's lower back.

10. A multi-segment supportive belt assembly in accordance with claim 9, wherein the weaving is a polypropylene weaving.

11. A multi-segment supportive belt assembly in accordance with claim 1, wherein the first linking segment includes a waist belt and the second linking segment includes a lower-back hips belt.

12. A multi-segment supportive belt assembly in accordance with claim 1, wherein the pivots connecting the second lateral segments to the second linking segment are located on the respective extremities of the second linking segment at a distance from each other such that when the multi-segment supportive belt assembly is worn by the user the pivots connecting the second lateral segments to the second linking segment are each positioned above the user's hip joint in a vertical plane and behind the user's hip joint in a horizontal plane.

13. A multi-segment supportive belt assembly in accordance with claim 1, wherein the pivots connecting the second lateral segment to the third linking segments are located on the third linking segments such that when the multi-segment supportive belt assembly is worn by the user the pivots connecting the second lateral segment to the third linking segments are each positioned at the user's hip joint in a vertical plane and behind the user's hip joint in the a horizontal plane.

14. A multi-segment supportive belt assembly in accordance with claim 1, wherein the pivots connecting the second lateral segment to the third linking segments are located on the third linking segments such that when the multi-segment supportive belt assembly is worn by the user the pivots connecting the second lateral segment to the third linking segments are each positioned at the user's hip joint in a vertical plane and in front of the user's hip joint in a horizontal plane.

15. A multi-segment supportive belt assembly in accordance with claim 1, wherein the cushions are made of neoprene.

* * * * *